United States Patent
Reicher et al.

(10) Patent No.: US 10,565,710 B2
(45) Date of Patent: Feb. 18, 2020

(54) SYSTEMS AND USER INTERFACES FOR DETERMINATION OF ELECTRO MAGNETICALLY IDENTIFIED LESIONS AS INCLUDED IN MEDICAL IMAGES OF DIFFERING PERSPECTIVES

(71) Applicant: INTERNATIONAL BUSINESS MACHINES CORPORATION, Armonk, NY (US)

(72) Inventors: Murray A. Reicher, Rancho Santa Fe, CA (US); Paul Dufort, Toronto (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/197,637

(22) Filed: Nov. 21, 2018

(65) Prior Publication Data

US 2019/0096065 A1 Mar. 28, 2019

Related U.S. Application Data

(63) Continuation of application No. 15/360,858, filed on Nov. 23, 2016.

(Continued)

(51) Int. Cl.
 *G06K 9/00* (2006.01)
 *G06T 7/12* (2017.01)
 *G06T 7/00* (2017.01)
(52) U.S. Cl.
 CPC .............. *G06T 7/12* (2017.01); *G06T 7/0014* (2013.01); *G06T 2207/10116* (2013.01); *G06T 2207/30068* (2013.01); *G06T 2207/30096* (2013.01)

(58) Field of Classification Search
 CPC ................ G06T 7/12; G06T 7/0014; G06T 2207/10116; G06T 2207/30068; G06T 2207/30096
 See application file for complete search history.

(56) References Cited

U.S. PATENT DOCUMENTS 6,748,044 B2   6/2004  Sabol et al.
7,809,175 B2 * 10/2010  Roehrig ................. A61B 6/463
                                            382/128

(Continued)

FOREIGN PATENT DOCUMENTS

WO     2008151113 A1    12/2008

OTHER PUBLICATIONS

Smith, A., "Fundamentals of Breast Tomosynethesis Improving the Performance of Mammography," in 8 pages.

(Continued)

*Primary Examiner* — Shefali D Goradia
(74) *Attorney, Agent, or Firm* — Michael Best & Friedrich LLP

(57) ABSTRACT

Systems and techniques are disclosed for determination of lesions identified in medical images of differing perspectives. One of the methods includes obtaining images of a breast of a patient, each image being from a perspective, wherein the images include at least a first image and a second image. A skin contour line representing an obliquity of a chest wall of the patient is determined. A posterior nipple line extending from a nipple included in the first image is determined that perpendicularly intersects with the skin contour line. An interactive user interface is presented that includes the posterior nipple line on the first image. Compatibility information for lesions indicated in each of the first and second image is determined, the information (Continued)

indicating whether a first lesion in the first image is a same lesion in the breast as a second lesion in the second image.

2 Claims, 9 Drawing Sheets

Related U.S. Application Data

(60) Provisional application No. 62/413,871, filed on Oct. 27, 2016.

(56) References Cited

U.S. PATENT DOCUMENTS

| | | | |
|---|---|---|---|
| 8,175,367 | B2 | 5/2012 | Chan et al. |
| 9,146,663 | B2 | 9/2015 | Kreeger et al. |
| 9,202,275 | B2 | 12/2015 | Ruth et al. |
| 2004/0015778 | A1* | 1/2004 | Britton ............... G06F 17/211 715/205 |
| 2004/0073132 | A1* | 4/2004 | Maahs ............... A61B 5/015 600/549 |
| 2005/0285853 | A1 | 12/2005 | Morita et al. |
| 2008/0155468 | A1 | 6/2008 | Rosander et al. |
| 2011/0194740 | A1 | 8/2011 | Khorasani |
| 2013/0028374 | A1 | 1/2013 | Gkanatsios |
| 2014/0355840 | A1 | 12/2014 | Pearson Peyton |
| 2018/0078231 | A1 | 3/2018 | Butani |

OTHER PUBLICATIONS

Non-Final Office Action from the U.S. Patent and Trademark Office for U.S. Appl. No. 15/360,858 dated Jun. 15, 2018 (12 pages).
Examiner-Initiated Interview Summary from the U.S. Patent and Trademark Office for U.S. Appl. No. 15/360,858 dated Sep. 28, 2018 (1 pages).
Notice of Allowance from the U.S. Patent and Trademark Office for U.S. Appl. No. 15/360,858 dated Sep. 28, 2018 (9 pages).
Oct. 27, 2016, U.S. Appl. No. 62/413,871.
Nov. 23, 2016, U.S. Appl. No. 15/360,858.

* cited by examiner und USER INTERFACES FOR DETERMINATION OF ELECTRO MAGNETICALLY IDENTIFIED LESIONS AS INCLUDED IN MEDICAL IMAGES OF DIFFERING PERSPECTIVES

CROSS-REFERENCE TO RELATED APPLICATIONS

Any and all applications for which a foreign or domestic priority claim is identified in the Application Data Sheet as filed with the present application are hereby incorporated by reference in their entirety under 37 CFR 1.57.

TECHNICAL FIELD

Embodiments of the present disclosure relate to systems and techniques for accessing one or more databases and providing user interfaces for dynamic interactions with medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Medical images are typically viewed by medical professionals, such as physicians, nurses, and so on, to determine proper diagnoses of patients. In general, the medical professionals can access medical images via physical copies of the medical images or via a display configured to present digital copies of the medical images. While reviewing a medical image of a patient, a medical professional can identify a lesion included in the medical image. For instance, the lesion may appear brighter or darker in the medical image or otherwise distort the expected normal anatomy. The medical professional may then scan through other medical images and attempt to similarly identify the same lesion in the other medical images. In this way, the medical professional can deduce a location of the lesion within a body part while viewing the lesion from various different vantage points.

SUMMARY

The systems, methods, and devices described herein each have several aspects, no single one of which is solely responsible for its desirable attributes. Without limiting the scope of this disclosure, several non-limiting features will now be described briefly.

Particular embodiments of the subject matter described in this specification can be implemented so as to realize one or more of the advantages discussed herein.

As will be described, this specification describes systems and methods usable to determine accurate posterior nipple lines (PNLs) in mediolateral-oblique images of a breast, for instance as taken during a mammogram. The specification describes technological improvements upon methods of determining PNLs, for instance methods that solely rely upon identifying a pectoralis major 'shadow' visible in a mediolateral-oblique image. The pectoralis major shadow can fail to provide accurate determinations of a PNL, as the shadow may (1) not be visible, (2) may be unclear as to the borders, (3) may fail to take into account the obliquity of the chest wall, and so on. Thus, this specification describes, for example, use of a 'skin contour line,' which can depend on particulars of breast margins and inflection points associated with the breast (e.g., anterior superior breast margin, posterior-inferior breast margin), and take into account obliquity of the chest wall. Additionally, the skin contour line can depend, or be modified according to, one or more offsets, which as described below can be based on a patient's age, body mass index, breast size/density, and so on.

After determining accurate posterior nipple lines (PNLs), accurate depth information associated with lesions (or other anatomical features of interest) indicated by medical professionals can be determined and compared. This specification further describes determining compatibility information between, for example, a lesion identified by a medical professional in a first image of a patient (e.g., a Cranial-Caudal image) and a lesion identified by the medical professional in a second image of the patient (e.g., a mediolateral-oblique image), with the compatibility information indicating whether finding identified in two or more images could correspond to a same lesion within the patient as well as optionally the probability of such compatibility. The invention further describes unique methods for calculating the location tolerance for determining compatibility, and the use of machine learning to determine such tolerances in relation to other image or patient characteristics, as well as determining compatibility probability based on image analytics (that evaluates image morphology, density, and other characteristics).

This specification further describes reducing complexities associated with notating lesions. As will be described, notating a lesion can include a medical professional describing features or labels of the lesion (e.g., benign, suspicious), location and/or depth information, and so on. Based on compatibility information, lesions can be determined to correspond to a same lesion, and thus a lesion being presently indicated by a medical professional on a medical image can be automatically selected as corresponding to a previously indicated, and optionally notated, lesion. Thus, the medical professional is not required to re-enter information for corresponding lesions, reducing errors associated with data entry.

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

As used herein, a Posterior Nipple Line (PNL) describes a line drawn on a mammogram posteriorly and perpendicularly from the nipple towards the chest wall (e.g., coronal plane) as has been described in the medical literature (as used herein, "mammogram includes digitized film mammograms, digital mammograms, breast tomosynthesis, and oblique views of the breast that could be derived from CT, MRI, 3D ultrasound, PET, or nuclear imaging). A PNL may be included in medical images (e.g., as an overlay) taken by imaging device(s) from disparate perspectives, such as mediolateral-oblique (MLO) images, cranial-caudal (CC) images, and so on, for example. As will be described, the system can receive user input from a medical professional (e.g., a doctor), and determine the PNL based on the user input. For example, a radiologist may identify a shadow of the patient's pectoral muscle in the medical image to estimate the location of the pectoral muscles and, thus, determine position of the PNL on an MLO view. Advantageously, this specification describes improved methods of calculated PNLs, such as based on skin contour lines that may be identified automatically by the computing system and/or indicated by the medical professional. The PNL provides a measure of the depth of a location in the breast.

As used herein, a Skin Contour Line is a line extending, in an oblique image of a breast, from the anterior superior breast margin to the posterior-inferior breast margin.

As used herein, a Pectoralis Major Shadow Line is a line associated with the depiction of the anterior margin of a patient's pectoralis major muscle, and can represent a demarcation between breast tissue and muscle.

As used herein, an enhanced PNL process is one in which a PNL is determined based on different markers within the medical image other than the pectoral muscles, resulting in an enhanced determination of a patient's coronal plane. For example, the skin contour line may be based on a determined inflection point above and/or below an imaged breast. Additionally, the enhanced PNL processes discuss herein may be calculated by computing systems that utilize machine learning techniques in order to determine more accurate locations of (1) skin contour lines, (2) PNLs, over time, such as based on medical professionals' feedback on whether calculated skin contour line and/or PNL determinations are accurate or inaccurate.

As used herein, compatibility information includes any information that can affect or inform a determination of whether locations in respective medical images (e.g., medical images of the same body part and patient obtained from different perspectives or from substantially the same perspective at different times) correspond to a same location within a body part, for instance based on depth (e.g., with respect to a posterior nipple line), location (e.g., from a landmark, such as an areola), and/or image characteristics.

Utilizing the enhanced PNL processing techniques discussed herein, for instance in an MLO image, the system can determine correlations between lesions included in different modalities of patient images, such as a CC and MLO images, for instance based on compatibility information. That is, the system can receive information (e.g., user input, as from a medical professional) indicating a location of a lesion in the CC image, and utilizing the enhanced PNL determined for the MLO image, can identify the same lesion in the MLO image.

As used herein, PNL modeling describes machine learning techniques wherein an algorithm for determining an enhanced PNL is updated as feedback from one or more sources is received and processed. For example, the system can receive information (e.g., user input from a medical professional) indicating that a lesion included in a CC image is the same as a lesion included in a MLO image, and can determine compatibility information indicating whether the lesions are likely the same based on depths of the lesions (e.g., with respect to the PNL). In this way, the system can aid medical professionals in determining proper diagnoses (e.g., a proper diagnosis associated with a mammogram), thus reducing cognitive errors. Furthermore, through the combination of active feedback from medical professionals (e.g., the medical professionals can indicate whether a determination of a PNL was accurate, or can indicate that the system's determination of incompatibility between two lesions is incorrect), the system can be updated, improving the functioning of the system for later use.

As used herein, PNL Factors are attributes that may be used as inputs to a PNL model in determining a skin contour line, calculating a PNL, and/or determining other PNL factors associated with a medical image. PNL factors may, for example, be used to determine offsets to be applied to a line extending from the anterior superior breast margin to the posterior-inferior breast margin. PNL factors may include, for example, a patient's weight, overall body measurements, breast measurements, presence of breast implants, imaging equipment attributes, user-specific attributes, and/or any other attribute that the PNL modeling (which may involve deep learning and image analytics), for example, determines may be helpful in determining more accurate PNLs. For example, a doctor may provide one or more of the PNL factors for a patient along with an assessment of a determined PNL and/or skin contour line (e.g., accurate, not accurate, distance of inaccuracy between modalities, etc.). These PNL factors can then be included in the machine learning performed by the PNL modeling to determine which PNL factors may affect accuracy of the PNL. These determined factors may then be implemented in the PNL model, such that they are determined prior to calculating a skin contour line, and used in the enhanced PNL process. PNL factors may be entered by a user (e.g., nurse, doctor, radiologist, etc.), accessed automatically from medical image data (e.g., DICOM header data), for another data source (e.g., a Customer Relationship Management (CRM) database), or any other data source.

Furthermore, the subject matter described in this specification solves problems arising out of use of technology. For instance, the subject matter described herein can advantageously provide corrections and updates to machine learning systems and machine learning techniques. Additionally, user interfaces can be improved through determinations of compatibility between lesions included in different medical images. As an example, the user interfaces can enable the succinct recording of notations related to the lesions, reducing a complexity associated with recording such notations and also use of user interfaces utilized to present medical images. For instance, upon determining that a particular lesion is included in two different medical images, a system can automatically generate notations associated with the particular lesion being in the medical images (e.g., locations within each image, location within the patient, and so on). Additionally, the user interface can automatically populate, and present, information about a lesion upon determining that the lesion is compatible with (e.g., matches) a lesion from a different medical image. Thus, the user interface can quickly present useful information to the medical professional (e.g., a label associated with the lesion from the different medical image, such as benign, probably benign, and so on), reducing a time the medical professional has to spend using the user interface (e.g., recording information about the lesion for each medical image). Notations that are presented may show a user that has marked a lesion in one view the most likely location(s) where the lesion may appear on one or more other views. Such notations may provide the user an indication of gradations of probability, such that a target area is presented where the lesion is most likely located with an indication of decreasing probability as the distance from the most likely target position is increased.

Embodiments of the present disclosure relate to systems and techniques for accessing data stores of medical images and displaying the medical images to efficiently provide information in an interactive user interface while providing functionality to a user of the interactive user interface (e.g., a medical professional). Previous systems for display of, and interaction with, image data were typically inefficient at presenting medical information. Disclosed herein are systems that, according to various embodiments, advantageously provide highly efficient, intuitive, and rapid dynamic interaction with medical images (including two-dimensional images and images rendered from three-dimensional image data). The systems may include interactive user interfaces that are dynamically updated to provide functionality to (1) identify a posterior nipple line (PNL) in each of the images, (2) determine whether lesions included in each image are the same lesions, (3) record notation information of lesions through use of user interface elements, and so on.

It has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including medical images) and may enable a user to more quickly and accurately access, navigate, assess, and digest the image data than previous systems, for instance based on compatibility information as described above.

Further, the interactive and dynamic user interfaces described herein are enabled by innovations in efficient interactions between the user interfaces and underlying systems and components. For example, disclosed herein are improved methods of receiving user inputs (including methods of interacting with, and selecting, images), translation and delivery of those inputs to various system components, automatic and dynamic execution of complex processes in response to the input delivery, automatic interaction among various components and processes of the system, and automatic and dynamic updating of the user interfaces (to, for example, display the relevant medical images). The interactions and presentation of data via the interactive user interfaces described herein may accordingly provide cognitive and ergonomic efficiencies and advantages over previous systems.

Various embodiments of the present disclosure provide improvements to various technologies and technological fields. Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic medical images, and presentation of the updates to displayed medical images via interactive graphical user interfaces. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data.

Additional embodiments of the disclosure are described below in reference to the appended claims, which may serve as an additional summary of the disclosure.

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, non-transitory computer-readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

Further, as described herein, various embodiments of the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

Figure 1A:
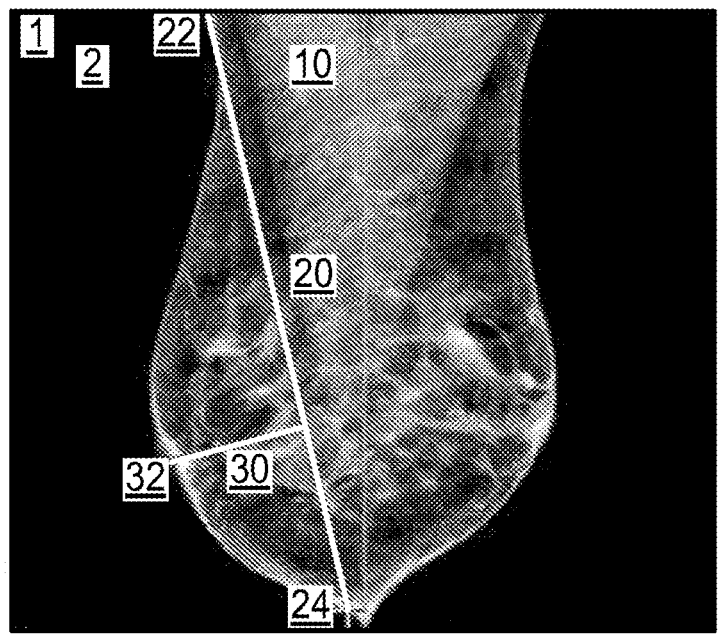
FIG. 1A illustrates an example user interface presenting a skin contour line included in a medical image of a body part.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

DETAILED DESCRIPTION

This specification describes systems and user interfaces for efficient and accurate determination of a posterior nipple line (PNL) in one or more medical images, such as images of an oblique mammogram (e.g., a mediolateral-oblique (MLO) image), with the PNL being a line extending posteriorly from the nipple to the posterior margin of the image perpendicular to the coronal plane. As will be described, for instance with respect to FIGS. 1A-1B, a PNL can be determined based on a proper identification of a skin contour line, which as will be described can be a line extending, in an MLO medical image, from the anterior superior breast margin to the posterior-inferior breast margin. The skin contour line can therefore improve upon methods of determining the PNL, for instance through approximating obliquity of the chest wall. Upon determination of the PNL for an MLO image, a depth along the PNL can be utilized to determine whether a lesion included in a first medical image (e.g., a CC image), and a lesion included in a second medical image (e.g., an MLO image), are the same lesion (e.g., likely to be the same lesion, that is a greater likelihood than a threshold) based on each lesion having a compatible depth along the PNL (e.g., PNL for the MLO image and PNL for the CC image). Although the embodiments described herein focus on the CC and MLO views, the same principles may apply to other views and other imaging modalities, including breast tomosynthesis, ultrasound, or MRI. In addition, the same principles can be applied to determine lesion compatibility in other body parts.

In this specification, medical images include any type of image of an organism (e.g., a human patient), and may include, but are not limited to, a radiograph (e.g., an x-ray image), computed tomography (CT), magnetic resonance imaging (MRI), Ultrasound (US), mammogram, breast tomosynthesis images, positron emission tomography scan (PET), nuclear medicine scans (NM), pathology, endoscopy, ophthalmology, and so on. While the specification below will describe the medical images as being images associated with a mammogram, the techniques herein can, in some cases, be used with other images for other purposes.

As will be described, a system (e.g., the medical analysis system 100 described below) can access one or more databases that store or maintain medical images of a patient (e.g., medical images associated with respective perspectives of the patient), and can (1) determine a posterior nipple line in particular medical images of the patient and (2) based on the determination, can determine compatibility information associated with lesions, seen (e.g., included in) the medical images, corresponding to the same lesion. In this specification, a perspective associated with an image includes a rotation of an imaging device with respect to a patient. For instance, a cranial-caudal image is a head to foot image (e.g., the imaging device captures an image of a body part, such as a breast, facing vertically downwards), while a mediolateral-oblique image is an angled side-view image (e.g., the imaging device is rotated and captures an image of the body part). The system can determine a mapping between the mediolateral-oblique image and the cranial-caudal image, with the mapping indicating a rotation of an imaging device in the mediolateral-oblique image. The rotation can be with respect to one or more bodily planes, such as with respect to a coronal plane of a patient.

As an example of determining a posterior nipple line, the system can present a particular medical image (e.g., an MLO image) in a user interface, and a user (e.g., a medical professional) can select particular locations on the presented medical image that inform a determination of a skin contour line. As described above, the skin contour line can extend from the anterior superior breast margin to the posterior-inferior breast margin, and the user can optionally select the endpoints of the skin contour line. The system can then determine the posterior nipple line as a line that extends from a nipple included in the particular medical image (e.g., the system can analyze the image, and determine a location of the nipple, or the system can receive a selection of the location, such as a centroid of the nipple) which perpendicularly intersects the skin contour line. Optionally, the system can analyze the particular medical image, and determine the skin contour line automatically (e.g., for confirmation by the user). An example of a user interface including a posterior nipple line is described below, and illustrated in FIG. 1A.

The determined posterior nipple line can be utilized by the system to inform a determination that a particular lesion included in a first medical image, corresponds with (e.g., is compatible with, such as compatible locations, depths, and so on, with the body part) a particular lesion included in a second medical image. As will be described, the system can present user interfaces to the user that include medical images, and the user can interact with the medical images (e.g., interact with a touch screen display, utilize a mouse, provide audio, such as speech, and so on) to identify locations of lesions (e.g., anomalies included in the medical images). The system can then determine compatibility information associated with the locations, which in this specification includes any information that can affect or inform a determination of whether locations in respective medical images (e.g., medical images associated with different perspectives) correspond to a same location within a body part, for instance based on depth (e.g., with respect to a posterior nipple line), location (e.g., from a landmark), and so on.

For example, the system can present a first medical image, and the user can select a location on the first medical image (e.g., touch a location, such as on a touch screen display) corresponding to a lesion. The system can then present user interface elements associated with notating the lesion (e.g., the user can describe features of the lesion, such as a label indicating whether the lesion is benign; location and/or depth of the lesion; and so on), and a notation can be generated and stored by the system (e.g., for inclusion, such as automatic inclusion, in a medical report). Examples of utilizing user interface elements to notate medical information, including through use of widgets that can advantageously present medical history information of patients, are described in U.S. patent application Ser. No. 15/253,746, titled "Automated Anatomically-Based Reporting of Medical Images via Image Annotation," which is hereby incorporated by reference in its entirety for all purposes.

The system can then present a second medical image (e.g., the user can request the second medical image, or the second medical image can automatically be displayed), and the user can select a location on the second medical image corresponding to a lesion. The system can analyze the selected location, and determine whether the location is compatible with the selected location in the first medical image. That is, the system can determine whether the locations can correspond to a same location within the patient, for instance based on respective depths relative to the posterior nipple line as included in the first medical image and second medical image.

As will be described, determining whether two or more marked findings are compatible (e.g., correspond to a same lesion in the same anatomical position), can be based on one or more configurable rules, which can optionally depend on information associated with the user (e.g., a user role, such as a type of doctor; seniority information, such as an amount of time and experience of the user, and so on). For instance, a rule can indicate depth tolerances required for the lesions to correspond to the same lesion. As an example, depths of two lesions included in respective medical images can be determined (e.g., based on the posterior nipple line), and a rule can specify a tolerance associated with the depths being compatible (e.g., the rule can indicate that the depths are required to be within a threshold distance of each other, such as 1 centimeter, and so on). As another example, the determined depths can be rounded, for instance to the nearest centimeter, and determined to be compatible upon the rounded depths matching. Optionally, a rule can indicate that tolerances can depend on distances of the lesions from the posterior nipple line and/or other landmark (e.g., nipple, areola). That is, for lesions located proximate (e.g., within a threshold distance of) the posterior nipple line and/or other landmark, the rule may require that the lesions be within a first threshold depth of each other, while for lesions located farther away, a rule may require that the lesions be within a second, greater, threshold depth of each other. The rule can optionally indicate that the tolerance (e.g., threshold depth) can be linearly, or non-linearly, proportional to a distance from the posterior nipple line and/or other landmarks.

Additionally, one or more rules can indicate whether the system is to automatically select two or more lesions as corresponding to a same lesion. For example, the user may indicate two lesions on a first medical image, and upon indicating a lesion on a second medical image that is compatible in depth with both the two lesions on the first medical image, a rule can indicate which of the two lesions on the first medical image is to be selected to correspond to the lesion in the second medical image. For instance, the rule can indicate that the system (1) is to select the lesion in the first medical image that has more recently been indicated, (2) is to analyze the morphology of each lesion, and select the lesion that has more compatible morphology with the lesion in the second medical image, (3) is to select the lesion that has an assigned label compatible with the lesion in the second image, with the labels including benign, probably benign, suspicious, and so on.

Optionally, a rule can be associated with warning (e.g., presenting information to the user describing a warning) the user that two or more lesions included in respective medical images are not compatible. For instance, the user can select a lesion in a first medical image as being compatible with a lesion in a second medical image, and a rule can indicate a tolerance associated with a probability of the lesions being compatible. Upon the system determining that the probability of the lesions being compatible is less than the tolerance (e.g., less than 1%, 2%, 10%, user-selectable probability), the system can provide information to the user indicating the likely incompatibility (e.g., present "less than 1 in 50 chance"). The probability can be updated as new information is received by the system, for instance the system can determine the probability based on machine learning techniques. As an example, a Gaussian process machine learning framework may be used in this context to both gather new data to adaptively refine its predictions, and also to produce probability measurements suitable for warnings to the user regarding lesion depth discrepancies.

In this way, the system can accurately determine compatibility information associated with two or more lesions corresponding to a same lesion. Optionally, the system can receive override information from the user, indicating that the system's determination is inaccurate (e.g., two lesions do indeed correspond to a same lesion, or two lesions do not correspond), and the system can update the rules or other techniques associated with determining compatibility information. Updating the system is described in more detail below, with respect to FIG. 6.

FIG. 1A illustrates an example user interface 1 presenting a skin contour line 20 included in a medical image 2 of a body part 10. The user interface 10 is an example of an interactive user interface that can be generated for presentation on a user device of a user (e.g., a laptop, a tablet, a computer, a wearable device, and so on), or can be generated by a system (e.g., the medical analysis system 100 described below) and presented on a display or user device (e.g., the system can generate a document, such as a web page, for presentation on the user device). As will be described, optionally a user device can be in communication with the system, and can generate user interface 1 (e.g., the user device can execute an application, or render information) and can receive information from the system for inclusion in the user interface 1.

In the example of FIG. 1A, the medical image 2 is a mediolateral-oblique (MLO) image of a breast 10, for instance as would be captured during a mammogram. To determine accurate locations of lesions within the breast 10, a posterior nipple line 30 can be utilized, with the posterior nipple line 30 extending from a nipple 32 to a patient's muscle (e.g., pectoralis major muscle). While a shadow may be visible within the medical image 2 as showing the anterior margin of the muscle in contrast to the breast 10 (e.g., pectoralis major shadow line), and utilized as a demarcation between the muscle and breast tissue, the shadow may not accurately model the obliquity of the chest wall. In this way, the posterior nipple line 30 extending from the nipple 32 to the muscle, may not accurately reflect a line perpendicular to the coronal plane.

Thus, as described above a skin contour line 20 can be preferred, or optionally combined with the pectoralis major shadow line (e.g., described below, with respect to FIG. 4), with the skin contour line 20 extending from the anterior superior breast margin 22 to the posterior-inferior breast margin 24. As illustrated in FIG. 1A, a user of the user interface 1 (e.g., a medical professional) can select the anterior superior breast margin 22 location and the posterior-inferior breast margin 24, and the system can determine a line connecting the locations 22, 24. For example, the user may interact with the user interface 1, for instance through touch interactions with a touch-screen displays, via a mouse, and so on, and the system can determine the locations 22, 24, based on the user interactions. Additionally, a touch-screen display presenting the user interface 1 may be sensitive to a force or pressure applied to the touch-screen display. Optionally, the user may press on the touch-screen display with a first force or pressure that corresponds to the anterior superior breast margin 22, and a second force or pressure that corresponds to the poster-inferior breast margin 24.

Upon determining the line connection locations 22, 24, the system can update the user interface 1 to present the skin contour line 20. As illustrated in the example, the skin contour line 20 can be a particular color (e.g., red, yellow, blue, and so on) that is distinct from colors utilized in the medical image 2 (e.g., black, white, such as in an x-ray). The user interface 1 can receive input to modify a location of the skin contour line 20, for instance the user may select one of the endpoints (e.g., locations 22, 24) and drag, or otherwise indicate movement of, the selected endpoint. The system can then update the user interface 1 to reflect the modified skin contour line 20. Optionally, the user can press on an endpoint with a particular pressure or force, and while pressing with at least that pressure or force, move the endpoint to a different location. Upon releasing the particular pressure or force, the endpoint may be moved and the user interface 1 updated. Optionally, the initially presented skin contour line 20 may remain while the user is moving an endpoint, with an updated skin contour line also presented. Upon the user releasing the particular pressure or force, the updated skin contour line 20 can remain while the initially presented skin contour line 20 may be removed. Optionally, to update the skin contour line 20, the user may be required to press harder than the particular force or pressure to confirm that the skin contour line is to be updated. In this way, the user can view differences between the skin contour lines, and accept an updated skin contour line when ready.

Optionally, the system may analyze the medical image 2 and determine the anterior superior breast margin 22 location and the posterior-inferior breast margin 24 location. For instance, the system can perform an initial edge detection process to identify edges associated with the medical image 2. As an example, the system can determine a skin contour of the breast 10, and optionally determine edges associated with features in the breast 10 such as the pectoralis major muscle and so on. The system can then select the anterior superior breast margin 22 as a location on the skin contour at a top portion of the image (e.g., the location may be determined to be above a curvature associated with the breast 2, for instance as illustrated in the example of FIG. 1A), and similarly select the posterior-inferior breast margin 24.

The analysis may be updated based on subsequent user interactions with medical images. For instance, the system can monitor modifications to the endpoints of the skin contour line 20 after the system analyzes the image and determines the locations 22, 24. The system can determine features included in medical images to be utilized when determining the locations 22, 24. For instance, the system can determine features of the skin contour (e.g., slope, distance from the nipple, distance from a pectoralis major muscle, and so on) to utilize in determining accurate locations 22, 24. Optionally, the system can utilize information associated with a patient whose medical image is being reviewed by the user, such as age, body mass index, breast size and/or density, and so on, to inform the automatic determination of the locations 22, 24.

Subsequent to determining, and presenting, the skin contour line 20, the system can determine the posterior nipple line 30 and update the user interface 1 to include a representation of the line 30. For instance, the posterior nipple line 30 can be presented in a particular color (e.g., a same color as the skin contour line 20, a different color, such as a complementary or opposite color, as the skin contour line 20, and so on). Optionally, the system can determine the posterior nipple line 30 through analyzing the image 2, and identifying the nipple 32 (e.g., the system can perform a feature recognition process). The system can then extend a line from the nipple 32 (e.g., a centroid of the nipple 32) that perpendicularly intersects with the skin contour line 20. Optionally, the user may select the location of the nipple 32, and the system can automatically determine the posterior nipple line 30 as extending from the location and perpendicularly intersecting with the skin contour line 20.

In this way, the posterior nipple line 30 may be accurately determined, and as will be described, utilized to determine whether lesions included in different images correspond to a same lesion within a patient (e.g., with the patient's breast).

Figure 1B:
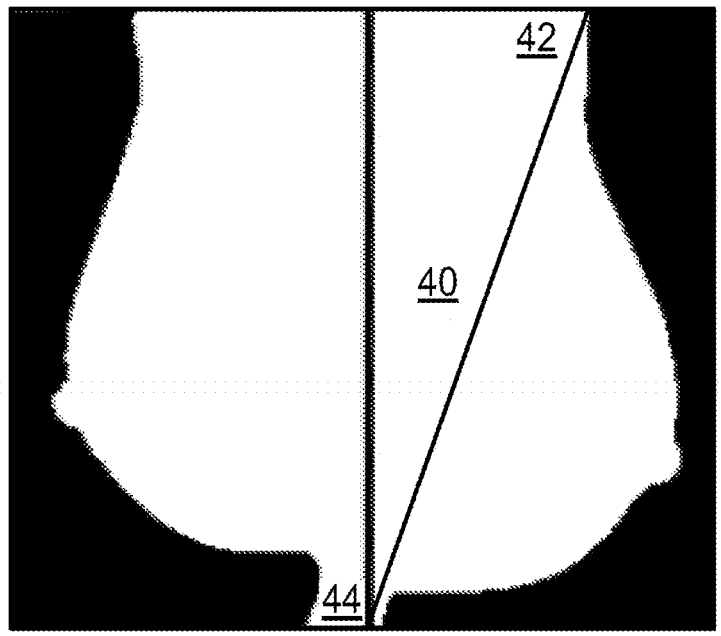
FIG. 1B illustrates another example of a skin contour line.

FIG. 1B illustrates another example of a skin contour line 40. The example of FIG. 1B includes a graphical representation of a body part, which in the example is a breast 46, and a skin contour line 40 extending from the anterior superior breast margin 42 location and the posterior-inferior breast margin 44. As illustrated, the skin contour line 40 extends from an upper portion of the breast skin contour (e.g., the highest portion included in the representation) to a lowest portion of breast skin contour.

Figure 2:
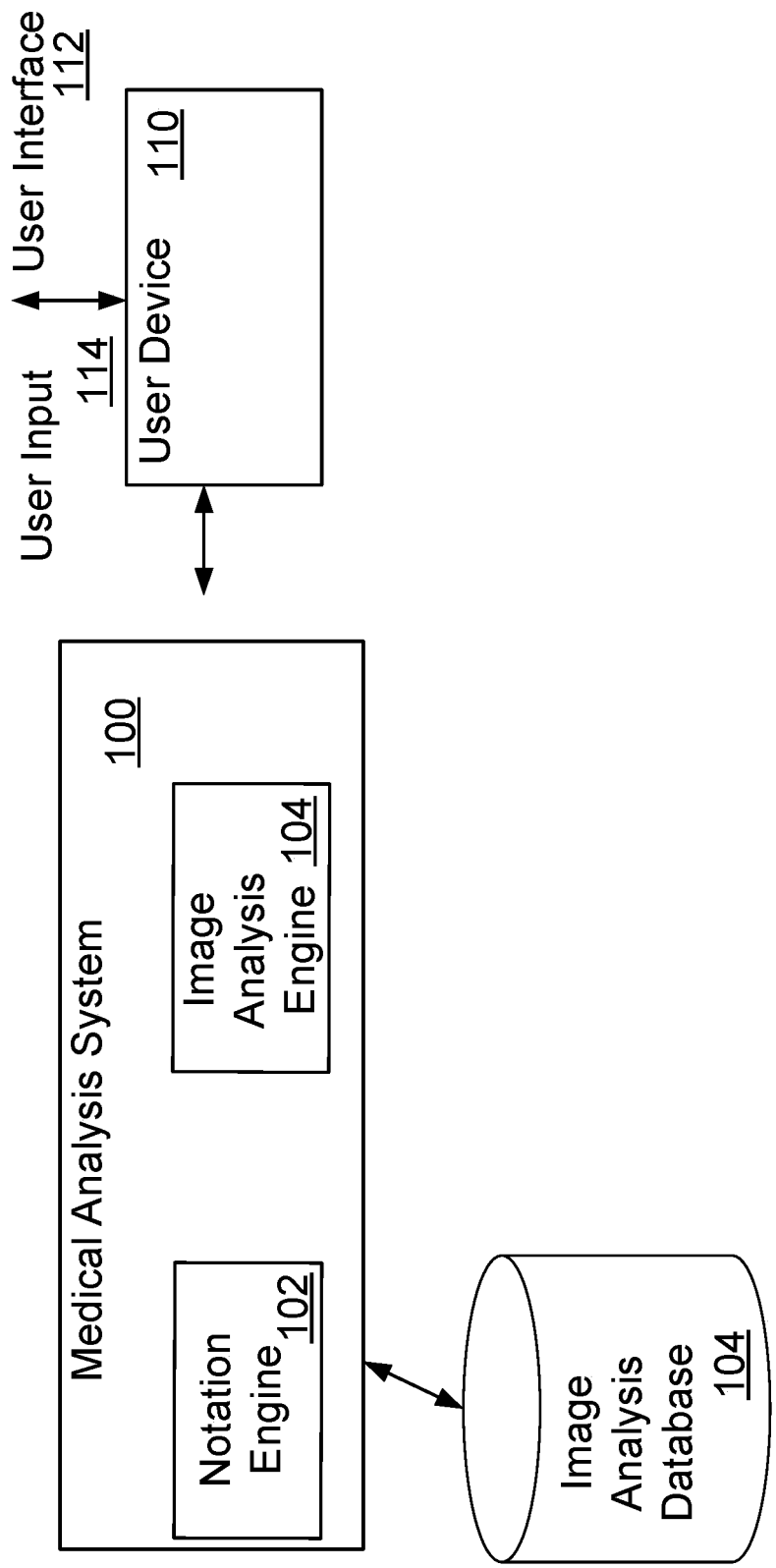
FIG. 2 illustrates an example block diagram of a medical analysis system in communication with other systems and components.

FIG. 2 illustrates an example block diagram of a medical analysis system 100 in communication with other systems and components. The medical analysis system 100 can be a system of one or more computers, or one or more virtual machines executing on a system of one or more computers, and can be in communication with a user device 110 (e.g., a user device comprising one or more hardware processors, such as a laptop, tablet, computer, or optionally a display in communication with the medical analysis system 100) and one or more databases 106 or storage subsystems (e.g., storing medical images of patients, medical histories of patients, medical reports, and so on).

As described above, the medical analysis system 100 can generate user interface information 112 for presentation on the user device 110, or optionally the user device 110 can generate user interface information 112 and receive information from the medical analysis system 100 for inclusion in the user interface 110. For instance, the user device 110 can execute an application, and present a user interface (e.g., the user interface 10 described above). The user device 110 can receive information from the medical analysis system 100, for instance information identifying skin contour lines, posterior nipple lines, medical information associated with a patient, such as previously notated lesions, and so on. Optionally, the user device 110 can perform some or all of the functionality of the medical analysis system 100 (e.g., the user device can determine a posterior nipple, and so on, and can optionally request that the medical analysis system 100 perform particular functionality, such as determining whether two or more lesions correspond with a same lesion, and so on).

To obtain medical images, the medical analysis system 100 can be in communication with, or optionally maintain, one or more databases or storage subsystems (e.g., the image analysis database 104), such that a user can cause presentation of medical images associated with a particular patient.

The medical analysis system 100 includes an image analysis engine 104 that can cause presentation of one or more medical images (e.g., stored in the database 104) in the user interface 112, and can receive user input 114 describing, or can determine, information relevant to determining whether lesions identified in the medical images correspond to the same lesion. For instance, the image analysis engine 104 can receive user input 114 describing a skin contour line to be presented in a medical image associated with a particular perspective (e.g., a mediolateral-oblique image), or the engine 104 can analyze the medical image and determine the skin contour line, and cause the user interface 112 to update with the skin contour line. The image analysis engine 104 can then determine a posterior nipple line, for instance as described above with respect to FIG. 1A, and update the user interface 112 to present the posterior nipple line. As will be described below, the image analysis engine 104 can optionally determine rotation information associated with the perspective, with the rotation information indicating a rotation of the imaging device with respect to a medical image of a different perspective (e.g., a rotation of the image device with respect to a Cranial-Caudal image). Additionally, the rotation information can indicate a rotation about a coronal plane, or other plane associated with a patient. That is, the rotation information can indicate a degree to which the imaging device was rotated (e.g., 30, 45, 60 degrees) with respect to the different perspective (e.g., Cranial-Caudal image, in which the imaging device faces vertically downwards).

The medical analysis system further includes a notation engine 102, which can enable notating lesions identified by a user in medical images. For instance, the user interface 112 can present a first medical image, and the user can provide user input to indicate that a particular location in the first medical image is associated with a lesion. As described above, the user can interact with a touch screen display of the user device 110, and describe features of the lesion such as whether the lesion is benign, a location and/or depth of the lesion, and so on. Additionally, the notation engine 102 can automatically determine the location and/or depth based on the user input. For instance, based on the determination of the posterior nipple line, the medical analysis system 100 can determine a mapping between images of different perspectives (e.g., a mapping between locations on a Cranial-Caudal image and on a mediolateral-oblique image). In this way, the notation engine 102 can automatically populate location and/or depth information for the lesion.

The notation engine 102 can further determine whether a lesion included in an image presently included in the user interface 112, is compatible with a lesion included in a different image, and can automatically indicate that the two lesions are the same (e.g., the notation engine 102 can record information indicating the lesion's being the same, for instance automatically updating a medical report, automatically populating information from a previously notated lesion, and so on). As described above, one or more rules can be associated with determining whether lesions correspond to each other, and can set tolerances associated with respective depths in a breast, and can indicate whether a presently selected lesion is to be automatically associated with a previously selected lesion. For instance, a rule can indicate that if a user selects a location of a lesion on a present medical image, and the lesion is compatible in depth (e.g., with respect to the posterior nipple line and/or other landmarks such as a nipple) with a lesion indicated on a prior medical image, the notation engine 102 can present information in the user interface 112 indicating the compatibility.

Optionally, the user interface 112 can be updated to present the prior medical image with the lesion highlight or otherwise identified (e.g., the prior medical image can be presented simultaneously with the present medical image, and optionally made smaller such as a 'picture-in-picture'). Examples and use of rules will be further described below, with respect to FIG. 5.

The medical analysis system 100 can utilize one or more machine learning models, or be in communication with an outside system associated with machine learning (e.g., a Watson based system), and can update any of the techniques and systems described above. For instance, the rules can be updated based on user input 114 of multitudes of users. As an example, a rule indicating that two lesions included in different medical images match if they are within a particular depth tolerance of each other can be updated based on monitoring user input confirming that the lesions match. The rule can be modified, for instance, based on determining that lesions which are further from the posterior nipple line and/or other landmark (e.g., nipple) are to be associated with greater depth tolerances. As an example, it the rule would normally indicate that two lesions included in different medical images do not correspond to a same lesion (e.g., based on their respective depths and a depth tolerance), upon monitoring user input indicating that the lesions do indeed match, the rule can be updated (e.g., updated upon a threshold number of times) to increase the depth tolerance. The particular locations of the lesions can be monitored, to additionally determine that the depth tolerances are to linearly increase as a distance from the posterior nipple line increases. Utilizing machine learning models will be described in more detail below, with respect to FIG. 6.

Figure 3:
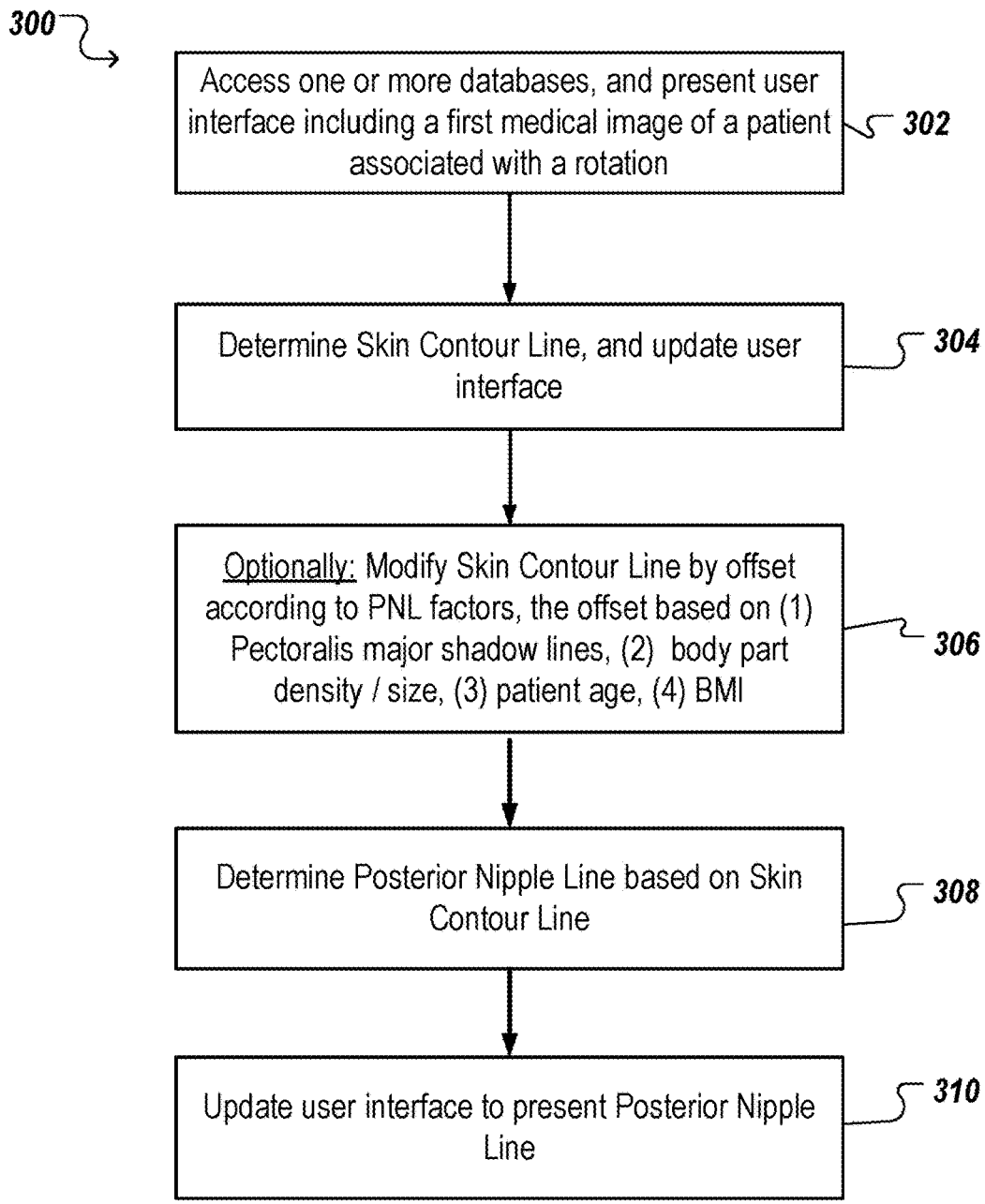
FIG. 3 illustrates an example flowchart of an enhanced posterior nipple line process.

FIG. 3 illustrates an example flowchart of an enhanced posterior nipple line process 300. For convenience, the process 300 will be described as being performed by a system of one or more computers (e.g., the medical analysis system 100).

The system accesses one or more databases, and presents a user interface including a first medical image of a patient, (block 302). As described above, a user can view a user interface presented on a user device (e.g., a tablet, a laptop, and so on) or via a display in communication with the system. The user can request the first medical image, for instance a first medical image from a mammogram, and review the first medical image.

The system determines a skin contour line, and updates the user interface (block 304). As described above, with respect to FIG. 1A, the system determines a skin contour line to present in the first medical image, for instance in a mediolateral-oblique (MLO) image, with the skin contour line extending from the anterior-superior point of the oblique breast skin contour to a posterior-inferior skin contour breast margin (e.g., the skin contour line can approximate the obliquity of the chest wall). The system can receive user input indicating endpoints of the skin contour line, and can present a representation of the skin contour line in the user interface. The system can then receive a confirmation that the skin contour line is accurate. Optionally, the system can analyze the first medical image, and determine the skin contour line (e.g., for confirmation by the user).

The system optionally modifies the skin contour line by one or more offsets (block 306). As described above, the skin contour line can represent an obliquity of the chest wall. To determine a correct posterior nipple line, the system can offset the skin contour line determined in block 304 according to one or more posterior nipple line (PNL) factors, such as information associated with the patient including patient age, body mass index, whether the patient has breast implants, breast size and/or density, and so on. The system, or an outside system associated with machine learning (e.g., a Watson system), can monitor skin contour lines indicated as being accurate by medical professionals. The system can then determine whether any offsets to the skin contour line are to be made, for instance the system can utilize features of the patient, and with a machine learning model (e.g., k-means clustering) can determine whether the features of the patient indicate that one or more offsets are to be applied. As an example, the system can determine that patients with high body mass indexes usually are associated with (e.g., greater than a threshold) skin contour lines that are modified by an offset (e.g., moved closer to a nipple or chest muscle, angled differently, have different endpoint locations, be non-linear such as a polynomial or other described curve, and so on).

Furthermore, as will be described in FIG. 4, the system may also modify the skin contour line according to a pectoralis major shadow line. That is, the system can determine whether the pectoralis major muscle is evident in the first medical image, and determine the pectoralis major shadow line that can approximate a boundary of the muscle, and modify the skin contour line according to the shadow.

The system determines the posterior nipple line based on the skin contour line (block 308). As illustrated in FIG. 1A, the system determines the posterior nipple line as a line extending from a nipple included in the first medical image that perpendicularly interests with the skin contour line. The system can update the user interface presented to the user, and can optionally receive confirmation from the user prior to storing information describing the posterior nipple line.

Figure 4:
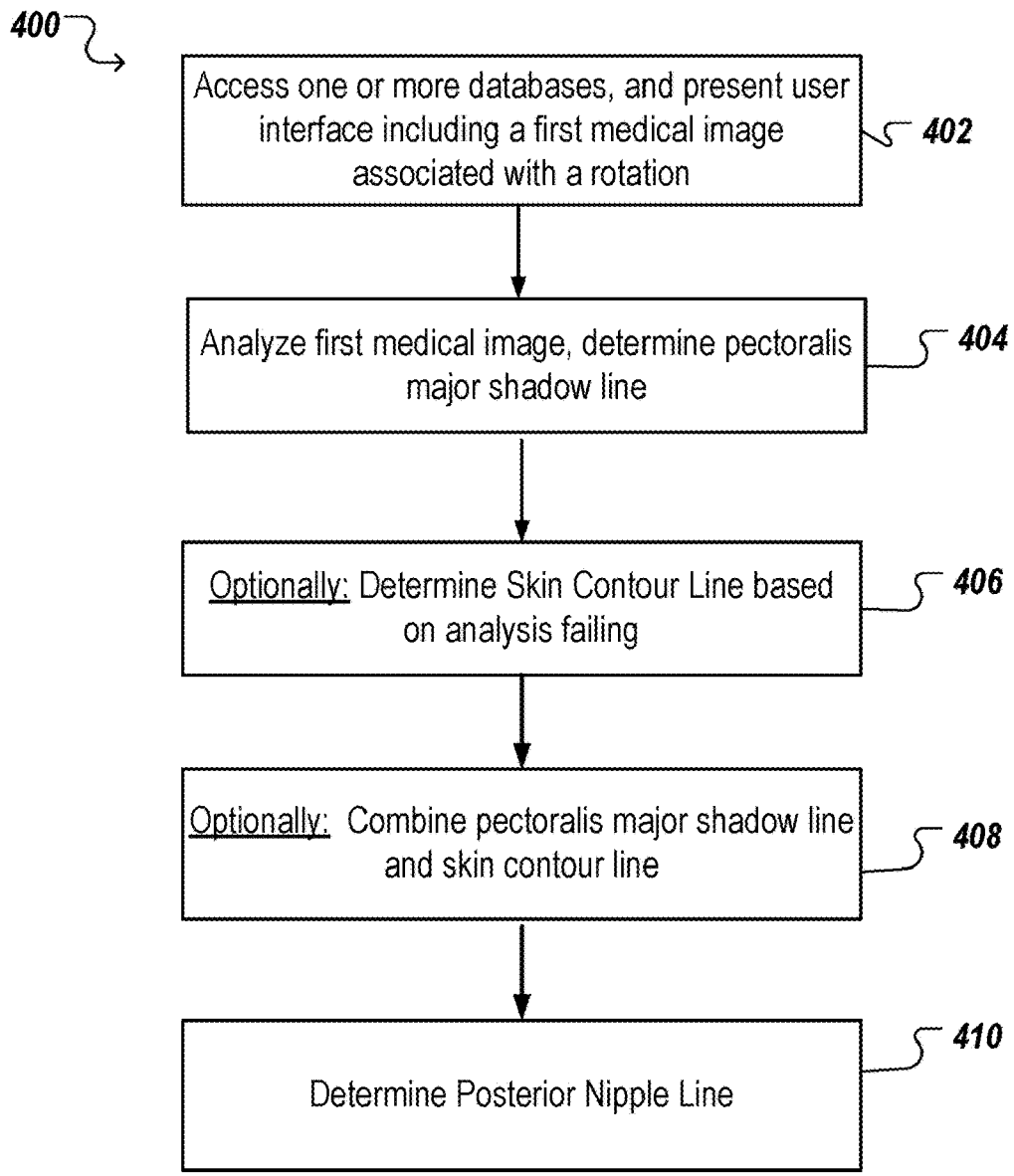
FIG. 4 illustrates another example enhanced posterior nipple line process.

FIG. 4 illustrates another example enhanced posterior nipple line process. For convenience, the process 300 will be described as being performed by a system of one or more computers (e.g., the medical analysis system 100).

The system accesses one or more databases, and presents a user interface including a first medical image associated with a rotation (block 402). As described above, the system can present the first medical image, which can be an MLO image associated with the imaging device being rotated.

The system analyzes the first medical image and determines a pectoralis major shadow line (block 404). The system can initially locate the pectoralis major muscle shadow, for instance based on a feature matching process on the first medical image or based on a color differential with respect to other portions of the breast (e.g., the shadow may appear as a lighter color than breast tissue, and darker than the muscle itself). The system can determine a shadow line based on the located muscle shadow, and can utilize the shadow line to determine a posterior nipple line.

For some medical images, a clear view of the pectoralis major muscle shadow may not be evident, and the system can then utilize the skin contour line (e.g., as described below with respect to block 406) or if the muscle shadow is evident, can combine the shadow line with the skin contour line (e.g., as described below with respect to block 408).

The system optionally determines the skin contour line based on failing to locate the pectoralis major shadow line (block 406). As described above, the system can initially attempt to locate the pectoralis major muscle shadow (e.g., based on image analytics, such as computer vision techniques as described above), and upon failing to locate the muscle shadow, can then determine the skin contour line for use in determining the posterior nipple line. Determining the skin contour line is described in more detail above, with respect to FIG. 1A and FIG. 3.

The system optionally combines the pectoralis major shadow line and skin contour line (block 408). As described above, the system can combine the shadow line and skin contour line in an effort to generate a more accurate line for use in determining the posterior nipple line. The system can utilize machine learning techniques, or receive information from an outside system associated with machine learning (e.g., a Watson system), to determine that the skin contour line is to be modified based on the shadow line. For instance, the skin contour line can be determined to be angled relative to the shadow line, or moved closer to, or further from, the shadow line. As an example, the system can monitor user input indicating whether a resulting posterior nipple line is accurate (e.g., a uses can modify a rotation associated with a posterior nipple line, and the system can determine that the skin contour line was inaccurate, and would be improved through combining the shadow line). Additionally, the skin contour line and shadow line can be averaged, or otherwise weighted and combined, to determine an updated line. As described above, with respect to FIG. 3, the skin contour line can further be modified according to information associated with a patient.

The system determines the posterior nipple line (block 410). The system determines the posterior nipple line as extending from a nipple included in the first medical image that perpendicularly intersects a line determined in any of blocks 404, 406, or 408.

Figure 5:
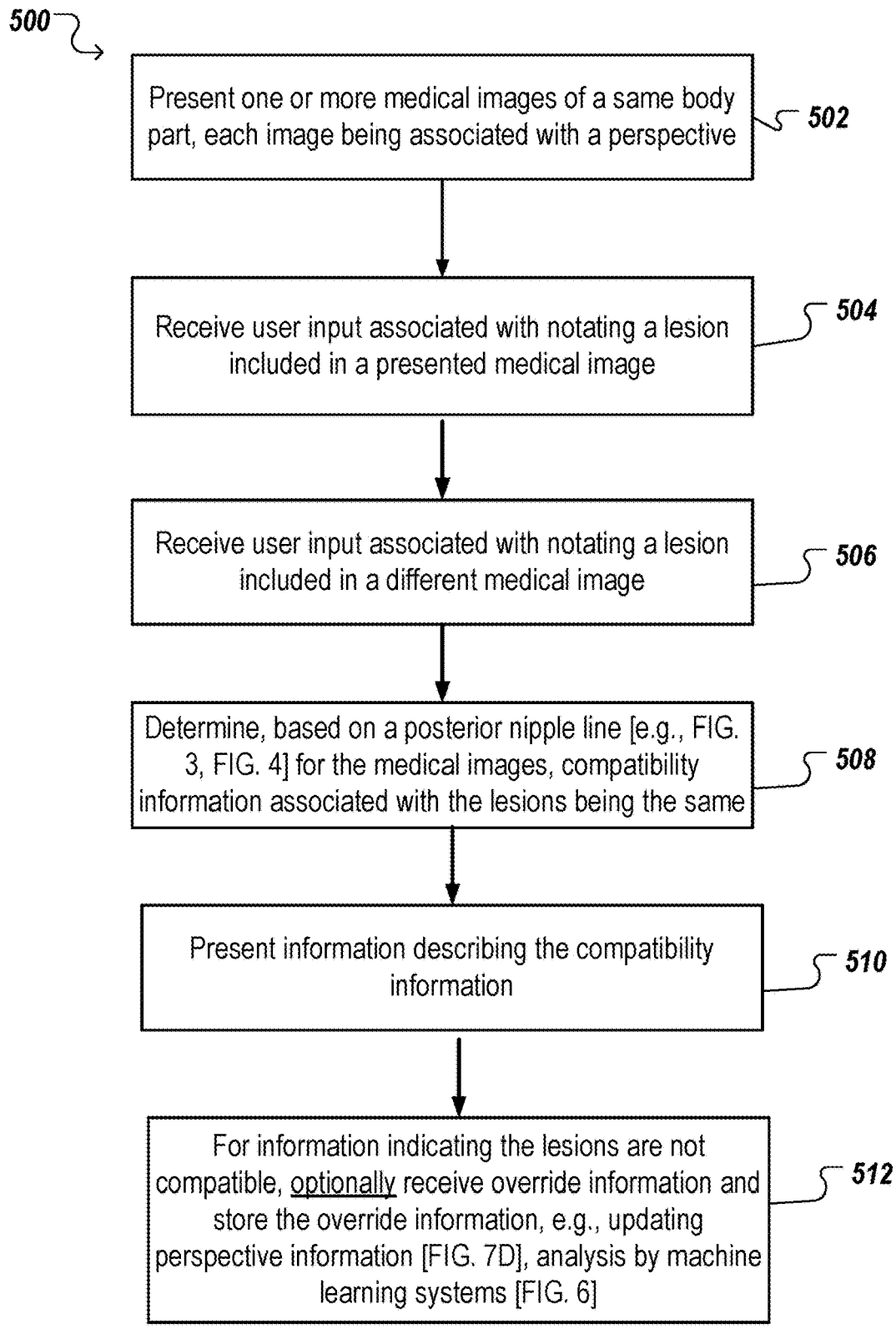
FIG. 5 illustrates an example process for determining compatibility information between lesions identified in different medical images.

FIG. 5 illustrates an example process 500 for determining compatibility information between lesions identified in different medical images. For convenience, the process 500 will be described as being performed by a system of one or more computers (e.g., the medical analysis system 100).

The system presents one or more medical images of a same body part (e.g., a breast) in a user interface, with each image being associated with a perspective (block 502). As described above, the medical images can be obtained during a mammogram of a patient, and can include different views (e.g., perspectives) of the breast. The views can include, for instance, a Cranial-Caudal view, a mediolateral-oblique view, a mediolateral view, a latero-medial view, and so on. Additionally, rotation information for the images can be determined, for instance a posterior nipple line can be determined for a mediolateral-oblique view, and a posterior nipple line can be determined for a Cranial-Caudal view (e.g., the line can extend perpendicularly from a nipple included in the Cranial-Caudal view to a pectoralis-major muscle). In this way, depth information for each of the views can be determined (e.g., based on the posterior nipple lines).

The system receives user input associated with notating a lesion included in a presented medical image (block 504). The user can select a location on the presented medical image corresponding to a location, and the user interface can update to include options associated with describing the lesion. For instance, the user can assign a label to the lesion (e.g., benign, probably benign, suspicious), can assign a depth and/or location of the lesion, or the system can automatically determine the depth and/or location and populate in the options, and so on.

The system receives user input associated with notating a lesion included in a different medical image (block 506). Similarly, the user can request, or otherwise receive, the different medical image, and select a location on the different medical image corresponding to the lesion.

The system determines compatibility information associated with the lesions corresponding to a same lesion (block 508). The system determines respective depths and/or locations of the lesions, for instance if the different medical image is a mediolateral-oblique image, the system can utilize a determined posterior nipple line to estimate a depth and/or location of the lesion (e.g., with respect to the posterior nipple line). The system can then determine a depth and/or location of the other lesion (e.g., the initially presented medical image can be a Cranial-Caudal image, and can similarly determine depth based on a posterior nipple line), and can determine whether the two lesions are compatible.

To determine depth and/or location information, the system can perform computations to localize the lesions in three dimensions, for instance based on the posterior nipple lines for the CC and MLO images. In one embodiment, the CC image can be positioned in the axial plane of the standard patient-based DICOM coordinate system (x increases from left-to-right, y increases from anterior-to-posterior, and z increases from inferior-to-superior), with the posterior edge of the image parallel to the coronal plane and the nipple at the origin. The MLO image can be initially positioned in the axial plane as well, with the posterior edge of the image parallel to the coronal plane and the nipple at the origin. The MLO image can then be rotated about the axial (inferior-to-superior) axis passing through the nipple until the respective posterior nipple lines coincide. The MLO image can then be rotated about the coronal (anterior-to-posterior) axis passing through the nipple to the angle specified in the DICOM attribute (e.g., Positioner Primary Angle if present), or to 45 degrees otherwise. Two infinite rays perpendicular to each view and passing through the lesion on each view can be defined. Since mammography creates projection images, these rays define the locus of possible 3D positions associated with the 2D positions identified on the image. By definition, these rays are parallel to the coronal plane. The closest approach distance between these two rays can define or indicate the depth compatibility. The two rays can be projected onto the coronal plane so that they intersect, and the point of intersection determined. The x- and z-coordinates of the 3D lesion position can be taken from the point of intersection, while the y-coordinate can be taken as the center of the closest approach line between the two rays. This is the mean of the depth of each lesion/ray along the PNL, measured from the nipple. From the lesion position in three dimensions, the depth and/or location information can be determined (e.g., depth category, clock angle, and quadrant defined in Breast Imaging Reporting and Data. System (BI-RADS) can be derived).

As described above, the system can maintain or otherwise receive (e.g., from a user), particular rules associated with determining compatibility information. For instance, the system can utilize a rule specifying a depth tolerance between the two lesions, with the depth tolerance indicating that the two lesions need to be at a depth within the depth tolerance (e.g., 0.5 cm, 1 cm). Additionally, a rule can indicate that the determined depths for each lesion are to be rounded to a nearest distance (e.g., nearest centimeter), or that the floor or ceiling of the depths are to be determined, and then compared. Similarly, as described above the depth tolerance can be based on one or more PNL factors, such as distances of the lesions from the posterior nipple line and/or other landmark (e.g., nipple) in respective medical images. In this way, the depth tolerance can be more stringent the closer the lesions are to the posterior nipple line, and more lax the farther away. The depth tolerance can also be based on other PNL factors, such as the viscoelastic and mechanical properties of the breast (e.g., these properties can inform or determine a degree of the breast's deformation under compression, such as during a mammogram) as represented by the tissue density indicated in the images. The tolerances may therefore depend on tissue density and texture properties mined from the images, through one or more image analysis techniques (e.g., color matching, for instance density can depend on a color, or a variation in colors).

Additionally, rules can be associated with determining which lesion corresponds to the lesion included in the different medical image. For instance, if the user indicated multiple lesions in block 504, and then indicated a lesion block 506, the system can determine which of the multiple lesions indicated block 504 can correspond to the lesion indicated in block 506. That is, a rule can indicate that if multiple lesions correspond according to a depth tolerance (e.g., a first lesion indicated in block 504 is within a depth tolerance of a lesion indicated in block 506, and a second lesion indicated in block 504 is within a depth tolerance of a lesion indicated block 506), then the more recently indicated lesion in block 504 is to correspond to the lesion indicated in block 506. That is, a rule (e.g., a rule set by the user, by an organization, and so on) can represent that the more recently indicated lesion is more likely to correspond to the lesion in block 506, as the user may be specifically trying to identify the matching lesion.

Furthermore, the system can analyze the lesions as depicted on the medical images, and determine morphology information associated with each lesion. For instance, upon selection of a lesion included in an image (e.g., as described in block 504), the system can utilize computer vision techniques to determine edges, shape, pixel intensity, color, pattern information, and so on, of a particular polygonal area (e.g., circle or oval) that surrounds the specified lesion. In this way, the system can compare the morphology information, and if two lesions in a particular image are potential matches with a lesion included in a different image (e.g., based on depth information), the system can determine a match based on the morphology information Similarly, the system can utilize information describing each lesion, for instance a label assigned the lesion by the user (e.g., benign, suspicious, or other characteristics of the lesions), and can determine compatibility between lesions based on the labels. That is, if two lesions in a medical image are indicated as being potential matches for a lesion in a different image (e.g., based on depth), the system can select one of the two lesions based on a label assigned to the lesion matching, or be more similar with, a label assigned to the lesion in the different image.

Furthermore, the system can receive input from the user indicating that the lesion identified in block 504 corresponds with the lesion identified in block 506. The system can then determine whether these lesions can correspond to a same lesion in the breast. For instance, the system can determine that, based on the depths of each lesion, the lesions are unlikely to correspond with each other (e.g., less a than a threshold percentage, with the percentage being determined according a difference in depth, which can depend on locations of the lesions with respect to the posterior nipple line and/or other landmark, and be informed based on empirical information from other users reviewing medical images). As will be described below, the system can then prompt the user to warn the user that the lesions are unlikely to correspond to a same lesion.

The system presents information describing the compatibility information (block 510). According to the compatibility information, the system can present information to the user describing whether the lesion indicated in block 504 is compatible with the lesion indicated in block 506. For instance, if the lesions are determined to be compatible (e.g., based on the rules), the system can auto-select the two lesions are corresponding to the same lesion. However, if the lesions are determined to be incompatible, the system can (1) present information to the user indicating the incompatibility, or (2) present nothing to the user. As described above, the user can specify that the two lesions are the same, for instance the user can assign a same name to the lesions, the user can manually indicate that the lesion indicated in block 506 corresponds to the lesion indicated in block 504, and so on, and the system can present compatibility information indicating (1) a probability of the lesions being the same, or (2) if the probability if less than a threshold, a warning to the user regarding the probability.

The user can optionally override a warning that the lesions are incompatible (block 512). As described above, the user can specify that the lesion indicated in block 504 is the same as the lesion indicated in block 506, and the system can optionally present a warning to the user upon determining that the lesions are unlikely to be the same (e.g., based on depth information). The user can optionally override the system, and indicate that the lesions indeed correspond to a same lesion with the breast.

This override information can be utilized by one or more machine learning models, and or by a machine learning system (e.g., Watson), to information subsequent determinations of probability of lesions corresponding. For instance, the override information from multitudes of users can be monitored, and utilized to inform subsequent determinations of depth tolerances, and so on.

Additionally, the system can optionally update a mapping between an image in block 504 and an image in block 506. For instance, a perspective associated with a mediolateral-oblique image may be updated based on the override information, as the posterior nipple line for the mediolateral-oblique image may have been incorrectly determined, for instance an angle and/or length associated with the posterior nipple line as it extends from the nipple. Thus, the system can determine that a rotation is to be made such that the lesions can be matched in depth. This can include modifying rotation information, perspective information, of the mediolateral-oblique image, modifying the posterior nipple line of the mediolateral-oblique image (e.g., modifying an angle associated with the posterior nipple line, such as modifying the skin contour line that intersects with the posterior nipple line, modifying a length of the posterior nipple line), and so on.

Figure 6:
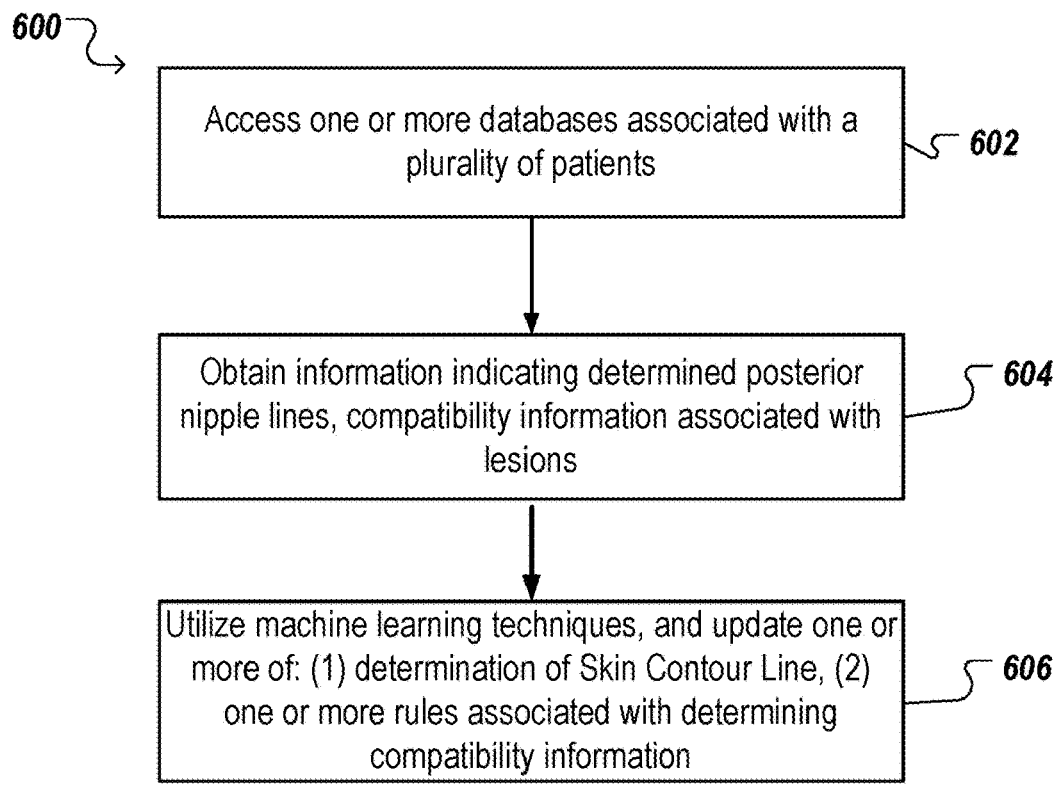
FIG. 6 illustrates an example process for utilizing machine learning techniques.

FIG. 6 illustrates an example process 600 for utilizing machine learning techniques. For convenience, the process 600 will be described as being performed by a system of one or more computers (e.g., the medical analysis system 100, or an outside system of one or more computers, such as a system associated with Watson).

The system accesses databases associated with a plurality of patients (block 602). The system can access information (e.g., anonymized information) from multitudes of mammograms or other procedures, the medical images of which having been reviewed by medical professionals.

The system obtains information indicating determined posterior nipple lines, compatibility information associated with lesions, and so on (block 604).

The system utilizes machine learning techniques and updates information for use in determining posterior nipple lines and/or compatibility information (block 606). As described above, the system can monitor whether determined skin contour lines are accurate, or whether, based on features of patients (e.g., age, body mass index, breast size/density), or pectoralis major muscle shadow lines, skin contour lines are to be modified. For instance, the system can utilize 'online' Gaussian machine learning techniques that can assimilate information immediately, or offline methods such as deep learning that can require periodic learning updates.

Additionally, the system can update rules for determining compatibility information, based on whether lesions determined by the system as being compatible were confirmed to be compatible by users (e.g., medical professionals). For example, tolerances, such as depth tolerances, can be improved upon based upon user input (e.g., whether lesions indicated as not being compatible based on depth tolerances, were confirmed to be compatible by medical professionals, and so on). Furthermore, as described in block 512, a determination may be made that rotation information associated with a mediolateral-oblique image is incorrect, and is to be updated based on respective depths of lesions. The system can monitor such determinations, and determine features associated with the determinations that can inform a more accurate determination of rotations (e.g., determine from determinations of posterior nipple lines). In this way, the system can inform the initial step of determining a skin contour line, as described above with respect to FIGS. 1A, 3-4. For example, the system can determine that the skin contour line is angled incorrectly, or is to be moved closer to, or further from, a muscle or nipple visible in medical images. Additionally, the system can determine that the skin contour line is to be combined with a pectoralis major shadow line, and can update the machine learning techniques accordingly. The determinations can further depend on features of patients, such as PNL factors, and the system can cluster patients according to feature, and optimize determinations of skin contour lines for each cluster.

Figure 7A:
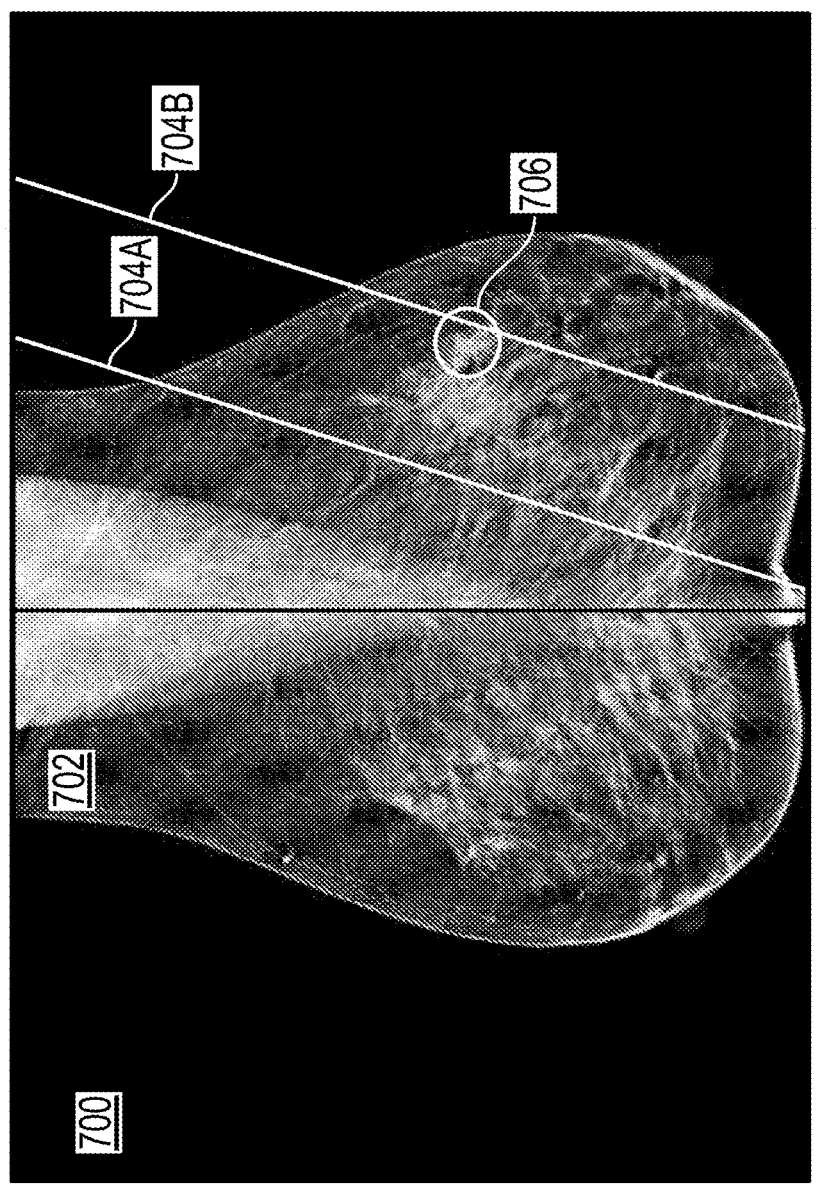
FIG. 7A illustrates an example user interface including a medical image associated with a perspective.

FIG. 7A illustrates an example user interface 700 including a medical image 702 associated with a perspective. The medical image 702 is an example of a mediolateral-oblique image, in which an imaging device was rotated to obtain the medical image 702. As illustrated, a user of the user interface 700 has indicated a particular lesion 706 illustrated in the medical image 702. Upon the indication, the user interface 700 can update to include lines 704A-704B that illustrates the predicted rotation (e.g., angulation) of the mediolateral-oblique image (e.g., with respect to a different image, such as a Cranial-Caudal image). In this way the user can get a sense of the rotation and perspective. As described above, the system can determine the rotation based on a determination of a posterior nipple line (e.g., as described above, with respect to FIG. 3).

Figure 7B:
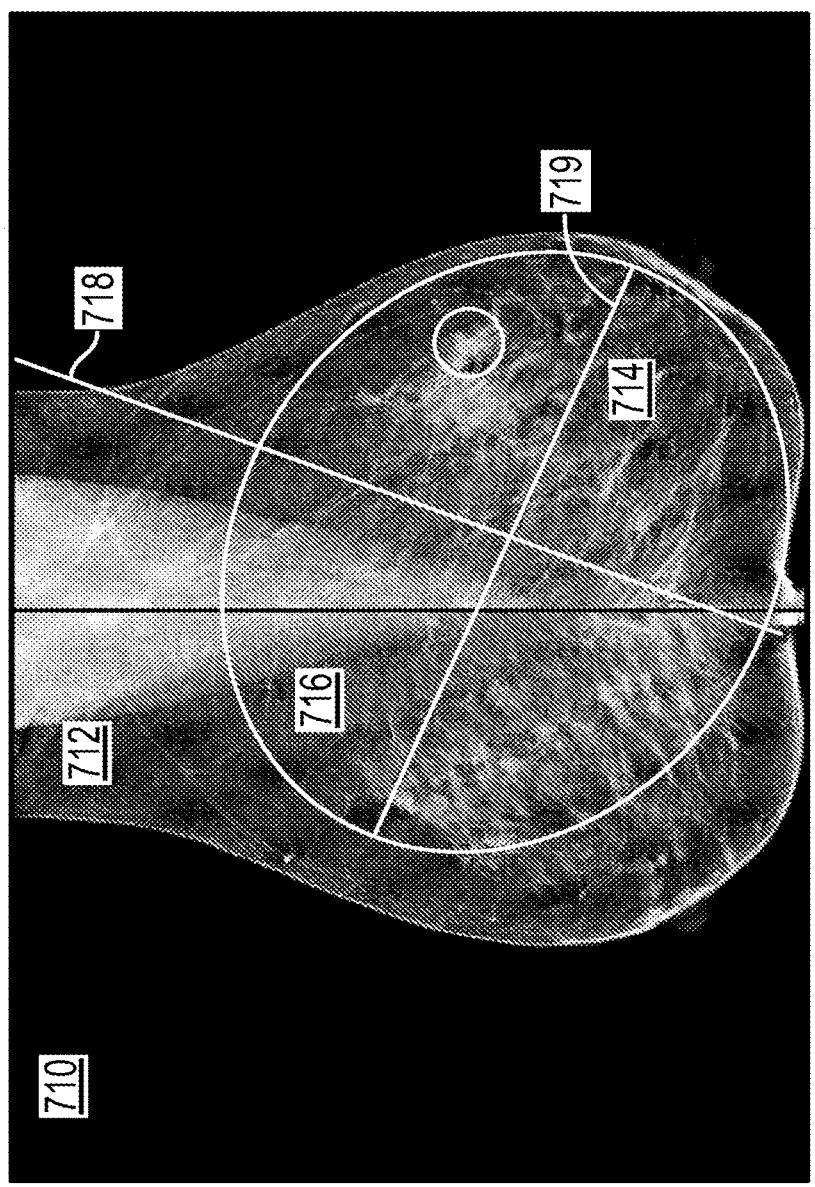
FIG. 7B illustrates an example user interface including a medical image associated with a perspective.

FIG. 7B illustrates an example user interface 710 including a medical image 712 associated with a perspective. The medical image 712 is an example of a mediolateral-oblique image, in which an imaging device was rotated to obtain the medical image 712. FIG. 7B illustrates another process of determining a posterior nipple line 714. To determine the posterior nipple line according to the illustration, a system (e.g., the medical analysis system 100) can determine an ellipse 716 that best fits the breast contour, and then determine a perpendicular line 718 through a centroid of the ellipse 716. The posterior nipple line 714 is then a line extending from the nipple 719 that perpendicularly intersects with the line 718.

Additional Embodiments

The system may analyze, present, and utilize, views in addition to the CC and MLO images described above. For example, once a lesion is marked on the CC and MLO, the system can predict the location on an LM or ML view. Similarly, if marked on a MLO and ML or LM view, the system can predict location on a CC view, or if marked on a CC and ML or LM view, the system can predict location on the MLO view. The ability to use two views to predict location on a third of fourth view can aide in diagnosis. Again, rules can be set for tolerances and other system behavior, such as if the system automatically displays the predicted location on a third view once two views are notated.

Optionally, a radiopaque line may be placed on an imaging device (e.g., on a compression paddle) or on a patient, and positioned in a coronal plane in order to mark the coronal plane on all mediolateral-oblique views. This line can be detected in the resulting medical image, and can be utilized to inform rotation information, or determination of rotation information or posterior nipple line, for the mediolateral-oblique image. Similarly, another plane or landmark can be marked when the patient is imaged in order to determine the coronal plane, axial plane, sagittal plane or other relevant reference point or plane.

Figure 7C:
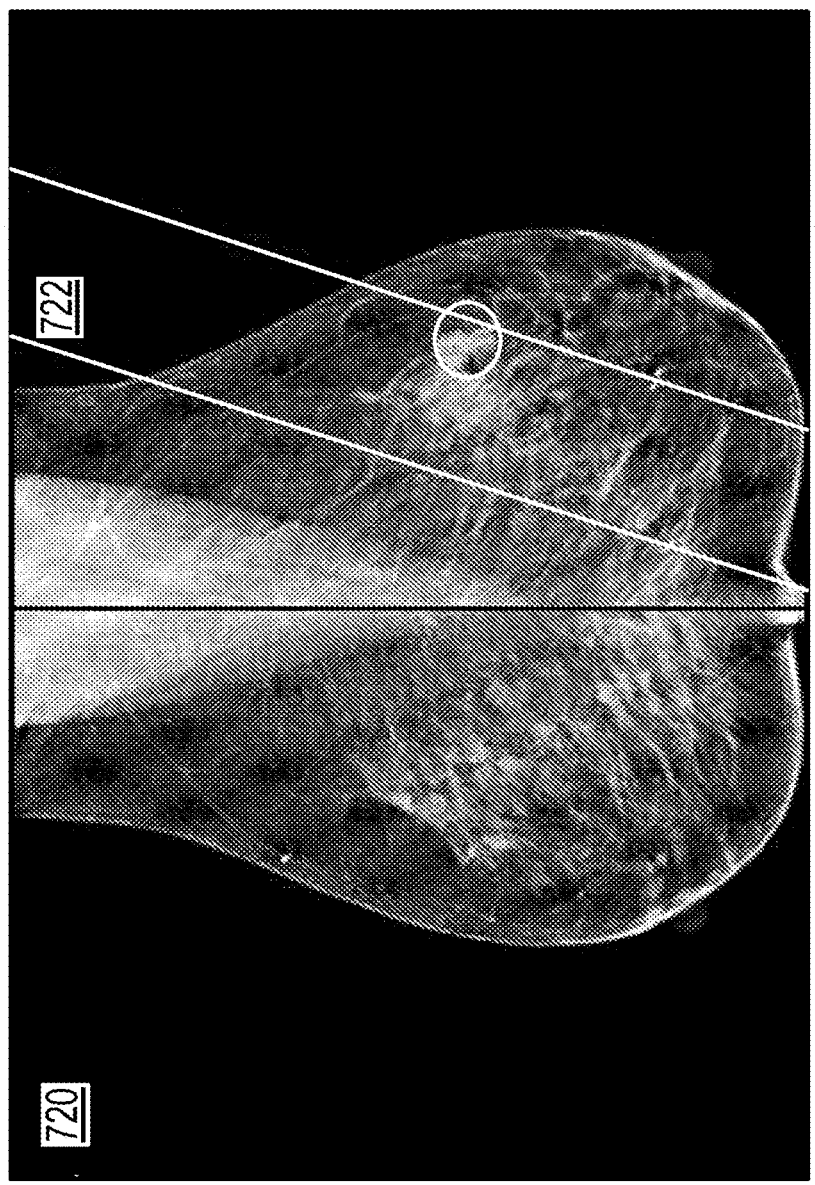
FIG. 7C illustrates an example user interface illustrating rotation information.

Optionally, while presenting a particular medical image associated with a perspective to a user (e.g., a medical professional), the system can present information indicating rotation information associated with a different perspective on the particular medical image. For instance, while presenting a Cranial-Caudal image, the system can graphically depict a perspective associated with a mediolateral-oblique image. As an example, the graphical depiction can include one or more lines angled on the Cranial-Caudal image, with the angled lines indicating a rotation about a coronal plane of an imaging device that captured the mediolateral-oblique image. Additionally, while presenting a mediolateral-oblique image, the system can graphically depict rotation information. For example, as illustrated in FIG. 7C, in one embodiment, when a user notates a lesion in the MLO projection, lines 722 may appear on an image that show the user the predicted angulation of the MLO projection by superimposing lines on the image. Furthermore, when a user notates a lesion on a particular medical image associated with a perspective, a medical image associated with a different perspective can be presented (e.g., as a 'picture-in-picture'), and an indication of the location of the lesion can be presented on the medical image associated with the different perspective).

Process descriptions, elements, or blocks in the flow diagrams described herein and/or depicted in the attached figures should be understood as potentially representing modules, segments, or portions of code which include one or more executable instructions (as described below) for implementing specific logical functions or steps in the process. Alternate implementations are included within the scope of the embodiments described herein in which elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved.

Any of the methods and processes described above may be partially or fully embodied in, and partially or fully automated via, logic instructions, software code instructions, and/or software code modules executed by one or more general purpose processors and/or application-specific processors (also referred to as "computer devices," "computing devices," "hardware computing devices," "hardware processors," and the like). For example, the methods described herein may be performed as software instructions are executed by, and/or in response to software instruction being executed by, one or more hardware processors (e.g., one or more processors of the computing system 150) and/or any other suitable computing devices. The software instructions and/or other executable code may be read from a tangible computer-readable medium. A tangible computer-readable medium is a data storage device that can store data that is readable by a computer system and/or computing devices. Examples of computer-readable mediums include read-only memory (ROM), random-access memory (RAM), other volatile or non-volatile memory devices, DVD-ROMs, CD-ROMs, magnetic tape, flash drives, and/or optical data storage devices. Accordingly, a software module may reside in RAM memory, flash memory, ROM memory, EPROM memory, EEPROM memory, registers, hard disk, solid state drive, a removable disk, a CD-ROM, a DVD-ROM, and/or any other form of a tangible computer-readable storage medium.

Additionally, any of the methods and processes described above may be partially or fully embodied in, and partially or fully automated via, electronic hardware (for example, logic circuits, hardware processors, and/or the like). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being redefined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method comprising:
   by one or more computer systems,
      obtaining a plurality of images of at least a portion of a same body part, each image associated with a different perspective of the body part, wherein the plurality of images include at least a first image and a second image;
      determining respective locations of an object included in each the plurality of images;
      determining, based on the respective locations and perspectives associated with the images, a mapping between the perspective associated with the first image and the perspective associated with the second image; and
      generating, for presentation in an interactive user interface, a graphical representation of the mapping, and presenting the graphical representation on the first image, wherein the graphical representation graphically indicates a degree to which an imaging device was rotated to capture the first image with respect to a position of the imaging device to capture the second image.

2. The method of claim 1, wherein a perspective includes a mediolateral-oblique perspective of the body part or a cranio-caudal perspective of the body part, and wherein the graphical representation indicates a rotation of an imaging device about one or more anatomical planes for the mediolateral-oblique perspective of the body part.

\* \* \* \* \*